(12) United States Patent
Bennett et al.

(10) Patent No.: US 11,059,353 B1
(45) Date of Patent: Jul. 13, 2021

(54) VEHICLE AIR FRESHENER

(71) Applicant: HOPKINS MANUFACTURING CORPORATION, Emporia, KS (US)

(72) Inventors: Kyle M. Bennett, Emporia, KS (US); Yafah Johnson, Simi Valley, CA (US); Pieter Schouten, Berkley, CA (US); Lynn Curtis Strong, Auburn, KS (US)

(73) Assignee: Hopkins Manufacturing Corporation, Emporia, KS (US)

( * ) Notice: Subject to any disclaimer, the term of this patent is extended or adjusted under 35 U.S.C. 154(b) by 25 days.

(21) Appl. No.: 16/519,072

(22) Filed: Jul. 23, 2019

(51) Int. Cl.
*B60H 3/00* (2006.01)
*A61L 2/00* (2006.01)

(52) U.S. Cl.
CPC .......... *B60H 3/0028* (2013.01); *A61L 2/0023* (2013.01)

(58) Field of Classification Search
CPC ................................ B60H 3/0028; A61L 2/23
USPC ............................................................ 239/54
See application file for complete search history.

(56) References Cited

U.S. PATENT DOCUMENTS

| 4,548,764 | A | * | 10/1985 | Munteanu | C11D 3/505 261/75 |
| 5,407,642 | A | * | 4/1995 | Lord | A61L 9/12 239/55 |
| 5,820,792 | A | * | 10/1998 | Lin | A61L 9/122 261/30 |
| 5,932,147 | A | * | 8/1999 | Chen | A61L 9/122 239/56 |
| 6,102,660 | A | * | 8/2000 | Lee | B60H 3/0028 416/146 R |
| 7,285,248 | B2 | * | 10/2007 | Yamamoto | A01M 29/12 422/123 |
| 7,559,108 | B2 | * | 7/2009 | Forte | A47L 25/005 15/104.002 |
| 8,784,747 | B2 | * | 7/2014 | Carmichael | A61L 9/04 422/306 |

* cited by examiner

*Primary Examiner* — Chee-Chong Lee
(74) *Attorney, Agent, or Firm* — Hovey Williams LLP

(57) ABSTRACT

An air freshener includes a housing; scented beads contained within the housing; and a mounting clip for attaching the housing to a source of pressurized air. The housing has several air flow slots or openings and is rotatably coupled to the mounting clip so it can be rotated relative to the mounting clip and the air source to which it is attached to provide several "levels" of fragrance, including a "burst" of fragrance achieved by manually rotating the housing relative to the mounting clip to tumble and stir the scented beads in the housing.

11 Claims, 8 Drawing Sheets

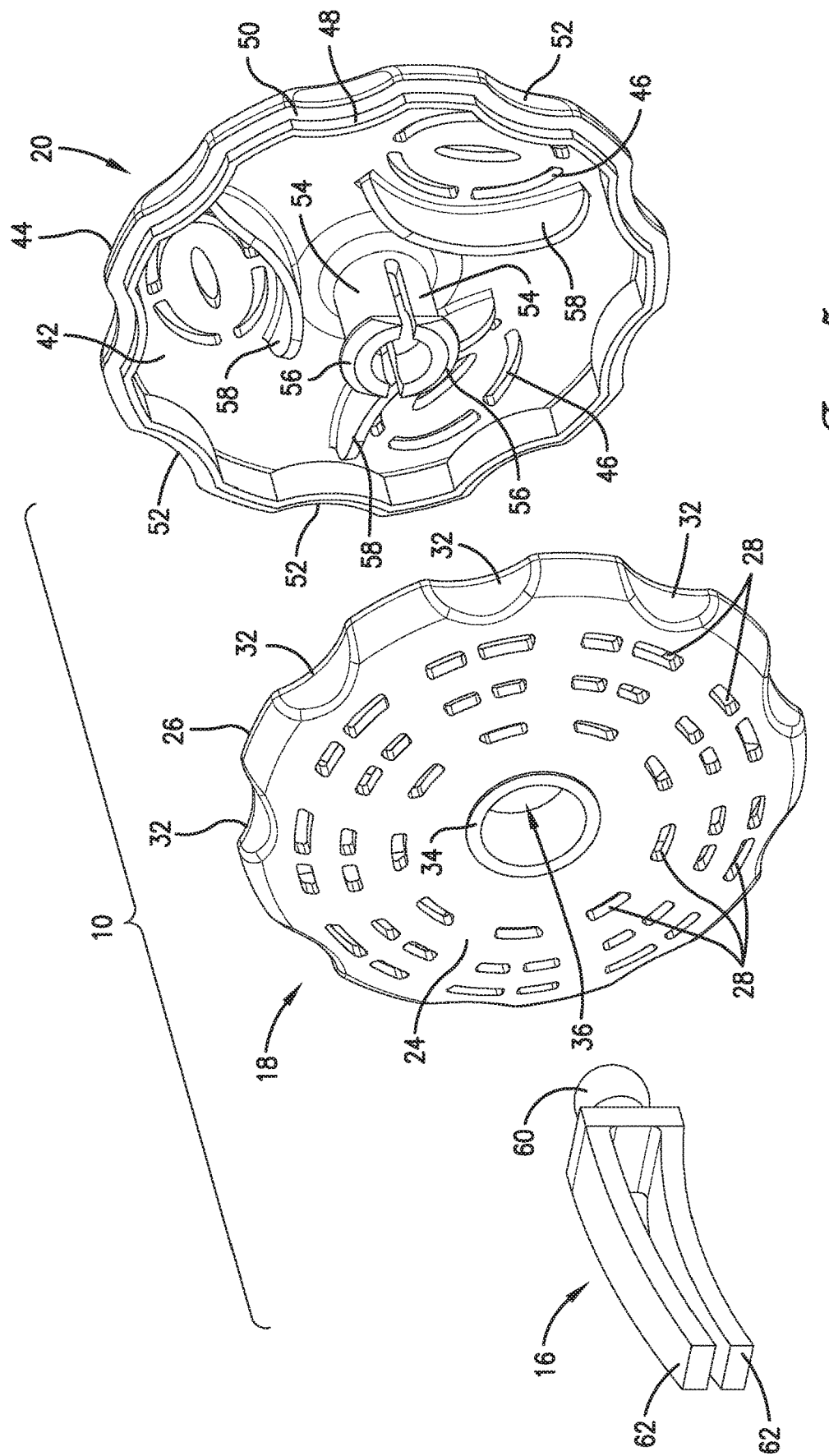

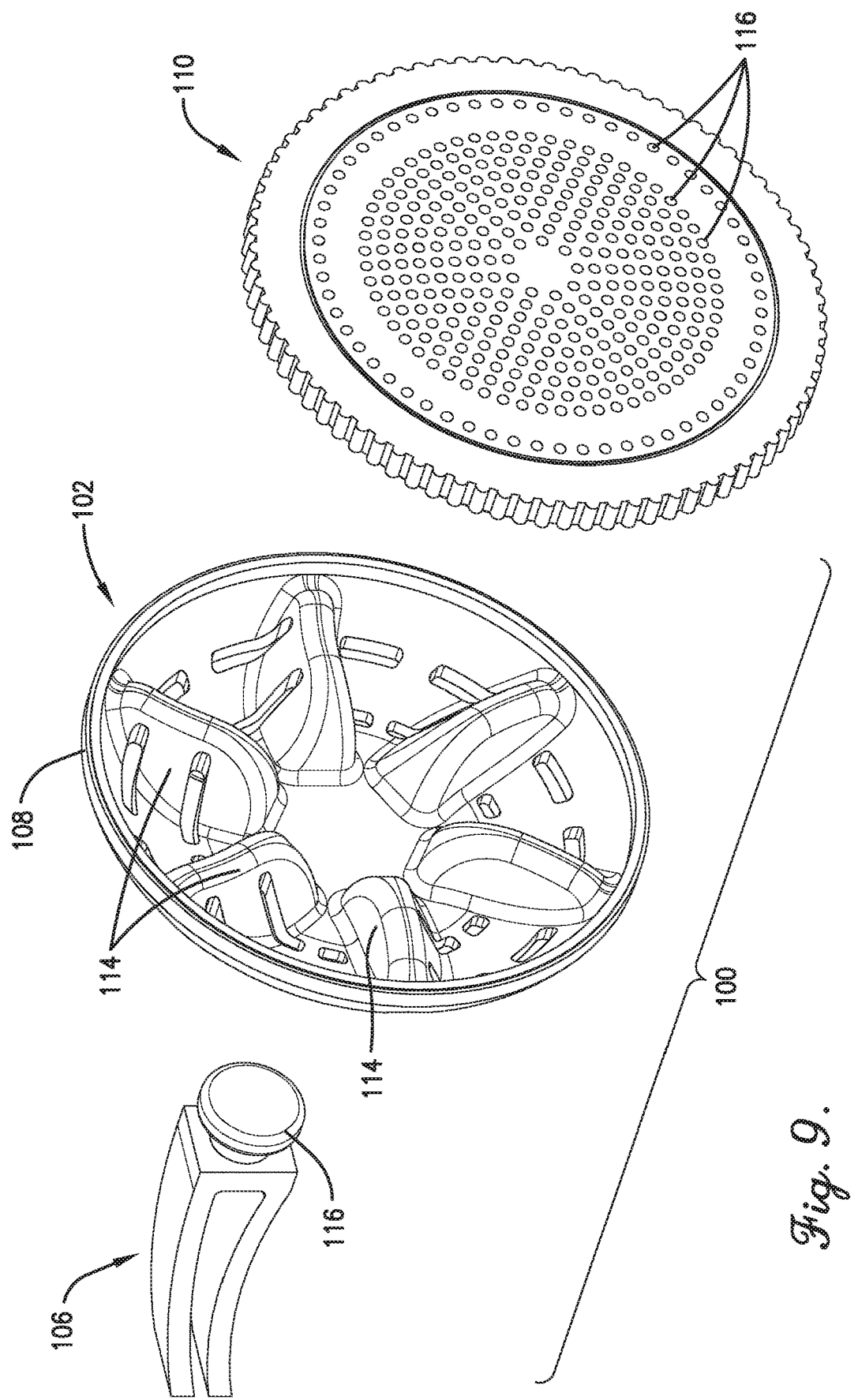

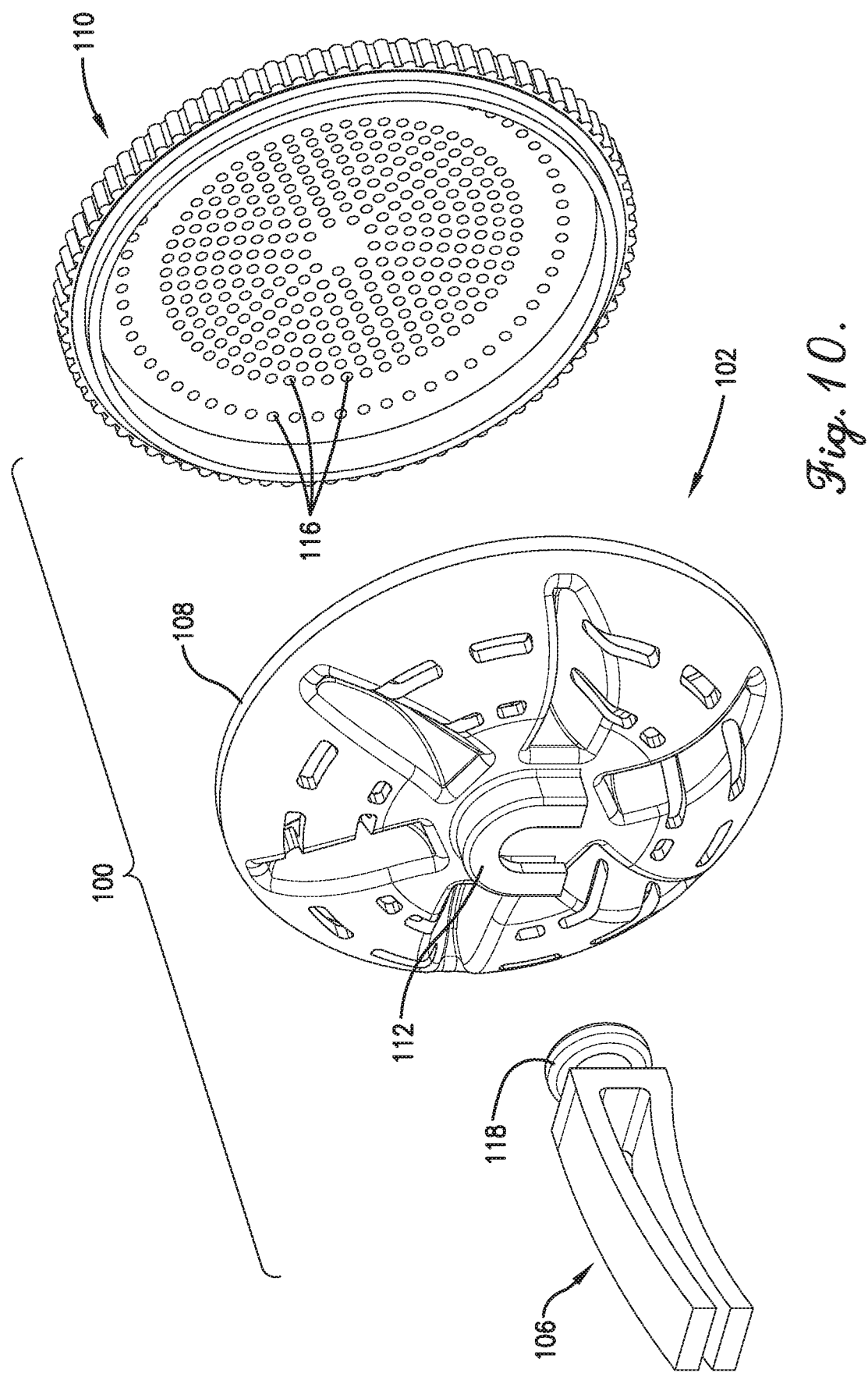

VEHICLE AIR FRESHENER

BACKGROUND

Air fresheners are often placed in vehicles and other places to mask odors and provide fragrance. One type of air freshener includes a semi-permeable pod, pouch, or other membrane in which liquid fragrance is partially sealed. The membrane allows the fragrance to slowly evaporate and diffuse within a vehicle compartment or other space. The fragrant-filled membrane may be supported next to an air vent by a housing and clip so that air discharged from the vent blows over the membrane and evaporates the liquid fragrant in the membrane. Unfortunately, these types of air fresheners only release noticeable amounts of fragrance when air is blown over them and are therefore only effective when vehicles' air conditioners or heaters are operated. More concentrated "blasts" of fragrance can be provided by aerosol spray type air fresheners, but these types of air fresheners often provide too much fragrance for relatively small vehicle compartments and are too big and clumsy for frequent vehicle use.

SUMMARY

The present invention solves the above-described problems and other related problems and provides a distinct advance in the art of air fresheners. More particularly, the invention provides an air freshener that provides a low-level of fragrance at all times and additional amounts of fragrance when desired without reliance on blown air or aerosol sprays.

An air freshener constructed in accordance with an embodiment of the present invention broadly comprises a housing; scented beads contained within the housing; and a mounting clip for attaching the housing to a vehicle air vent or other source of pressurized air. The housing has several air flow slots or openings and is rotatably coupled to the mounting clip so it can be rotated relative to the mounting clip and the air source to which it is attached. The air freshener provides a first relatively low level of fragrance constantly as fragrance evaporates from the scented beads and exits the openings in the housing even when the housing and enclosed beads are not subjected to any air flow. A second relatively higher level of level of fragrance is provided when pressurized air from an air vent or other air source blows over and through the housing to accelerate the evaporation of fragrance from the scented beads. A third level or "burst" of fragrance may be provided by manually rotating the housing relative to the mounting clip to tumble and stir the scented beads in the housing to expose the scented beads to more air and thus release more fragrance. The third level of fragrance is even greater if the housing is rotated while a pressurized air is blown over and through the housing.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 5 is an exploded, rear perspective view of the air freshener of FIG. 1.

FIG. 9 is an exploded, front perspective view of the air freshener of FIG. 6.

FIG. 10 is an exploded, rear perspective view of the air freshener of FIG. 6.

Figure 2:
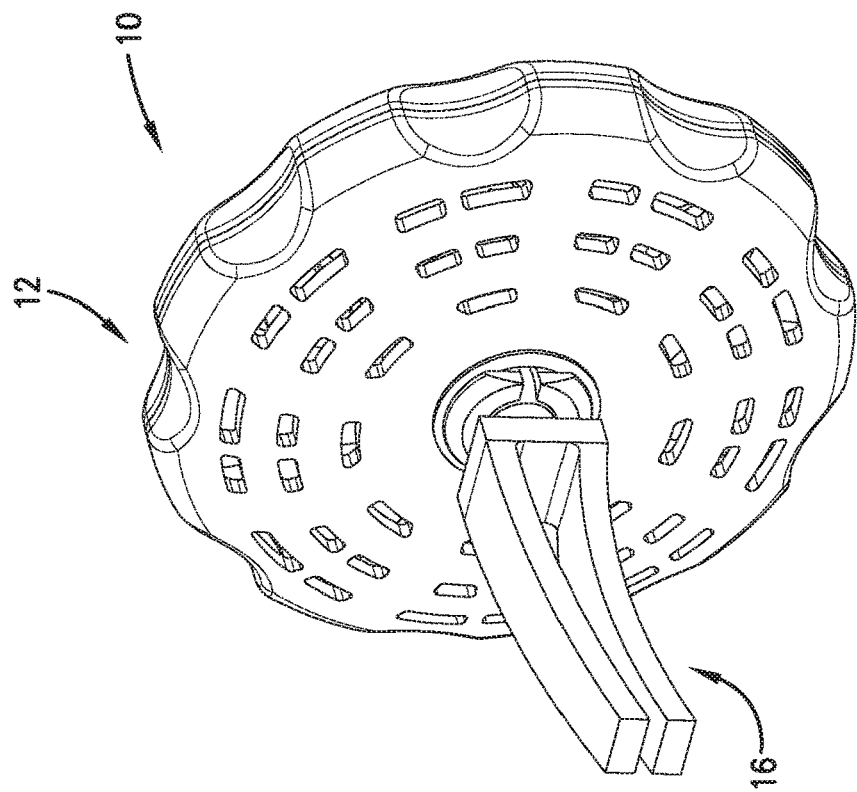
FIG. 2 is a rear perspective view of the air freshener of FIG. 1.
Figure 1:
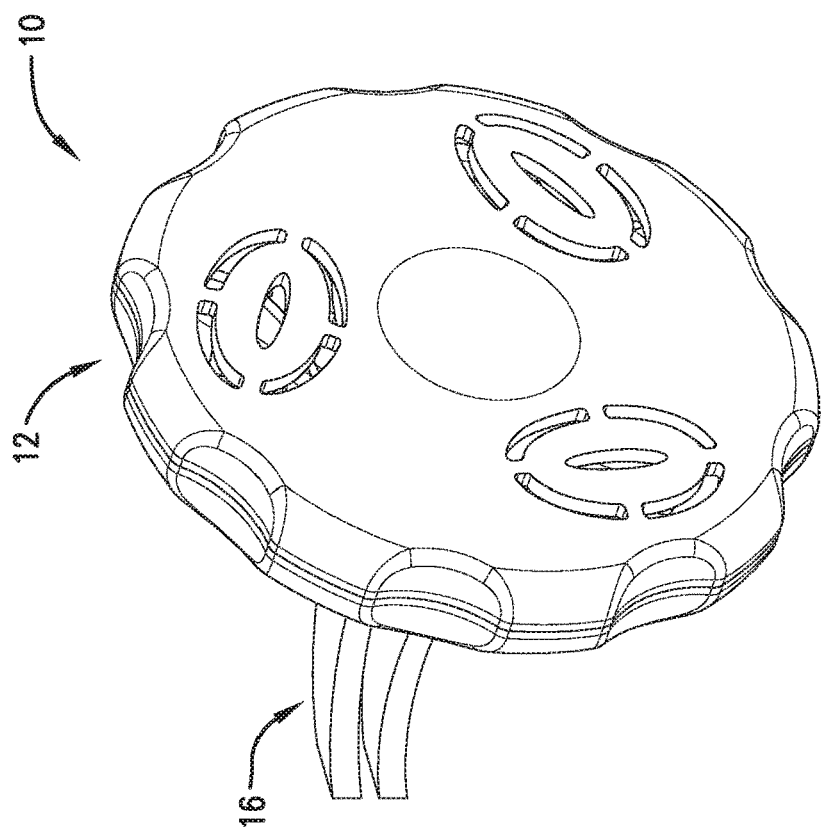
FIG. 1 is a front perspective view of an air freshener constructed in accordance with an embodiment of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings. The embodiments are intended to describe aspects of the invention in enough detail to enable those skilled in the art to practice the invention. Other embodiments can be utilized, and changes can be made without departing from the scope of the claims. The following detailed description is, therefore, not to be taken in a limiting sense. The scope of the present invention is defined only by the appended claims, along with the full scope of equivalents to which such claims are entitled.

Figure 3:
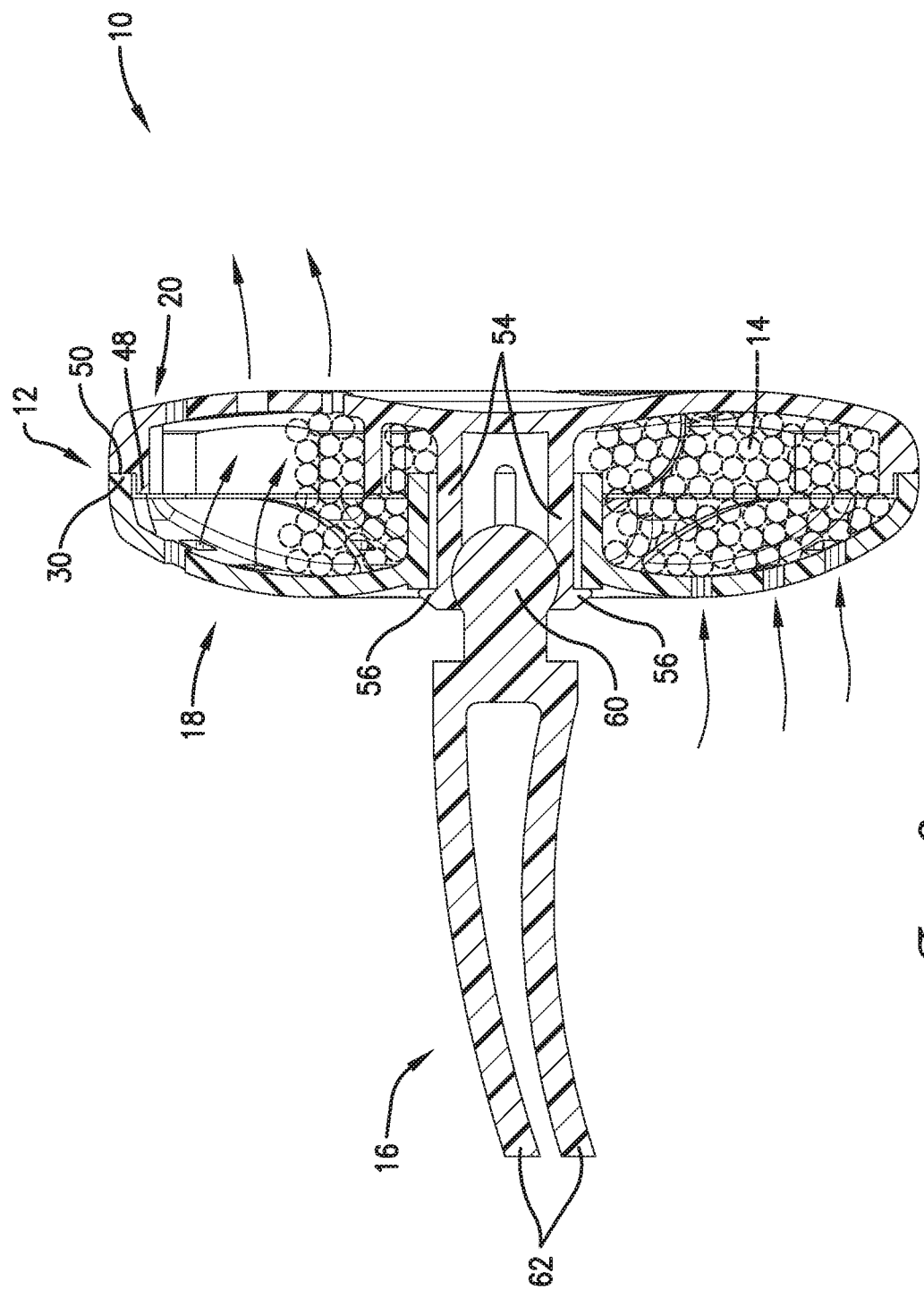
FIG. 3 is a vertical side sectional view of the air freshener of FIG. 1.

An air freshener 10 constructed in accordance with a first embodiment of the invention is shown in FIGS. 1-5. The air freshener is especially suited for use in a vehicle but may be used anywhere. As best shown in FIG. 3, the air freshener 10 broadly comprises a housing 12; scented beads 14 enclosed in the housing; and a mounting clip 16 for attaching the housing 12 to a vehicle air vent or other source of pressurized air.

The scented beads 14 are conventional and will therefore be described first. The scented beads, also sometimes called aroma beads, are small semi-absorbent beads soaked in fragrant oil. The beads may be formed of translucent plastic or other semi-absorbent materials and may be any shape and size. The fragrant oil slowly evaporates from the beads to release fragrance into the surrounding air. Any type of scented beads can be used without departing from the scope of the invention. For example, the scented beads may be formed of materials other than plastic and/or may be soaked in fragrances other that fragrant oils. Scented beads suitable for the present invention may be purchased from multiple sources.

The housing 12 encloses the scented beads 14 and exposes them to air flow as described in more detail below. An embodiment of the housing is formed of plastics or other suitable materials, is disc-shaped, and is approximately 1"-1.5" in diameter and ⅛-¾" thick. However, the housing may be formed of any materials and in any shape or size without departing from the scope of the present invention. As best illustrated in FIGS. 4 and 5, an embodiment of the housing 12 includes a rear housing section 18 and a front housing section 20 that are joined together to form a partially hollow chamber in which the scented beads 14 are contained.

The rear housing section 18 includes front and rear faces 22, 24 and a sidewall 26 between the faces 22, 24. Airflow slots or openings 28 extend between the faces 22, 24 for permitting air to pass through the housing. The slots or openings 28 are small enough to retain the scented beads 14 within the housing but large enough and in sufficient quantity to allow air into and out of the interior chamber of the housing. In one embodiment, the slots or openings 28 are arranged in three concentric rings around the center of the rear housing section and occupy 20-50% of the surface area of the rear face 24.

The sidewall 26 of the rear housing section 18 includes an outer lip 30 or edge best shown in FIGS. 3 and 4 for coupling with the front housing section 20 as described in more detail below. The sidewall 26 also includes indents 32 spaced around its perimeter that mate with similar indents in the front housing section to form grips for facilitating rotation of the housing.

Figure 4:
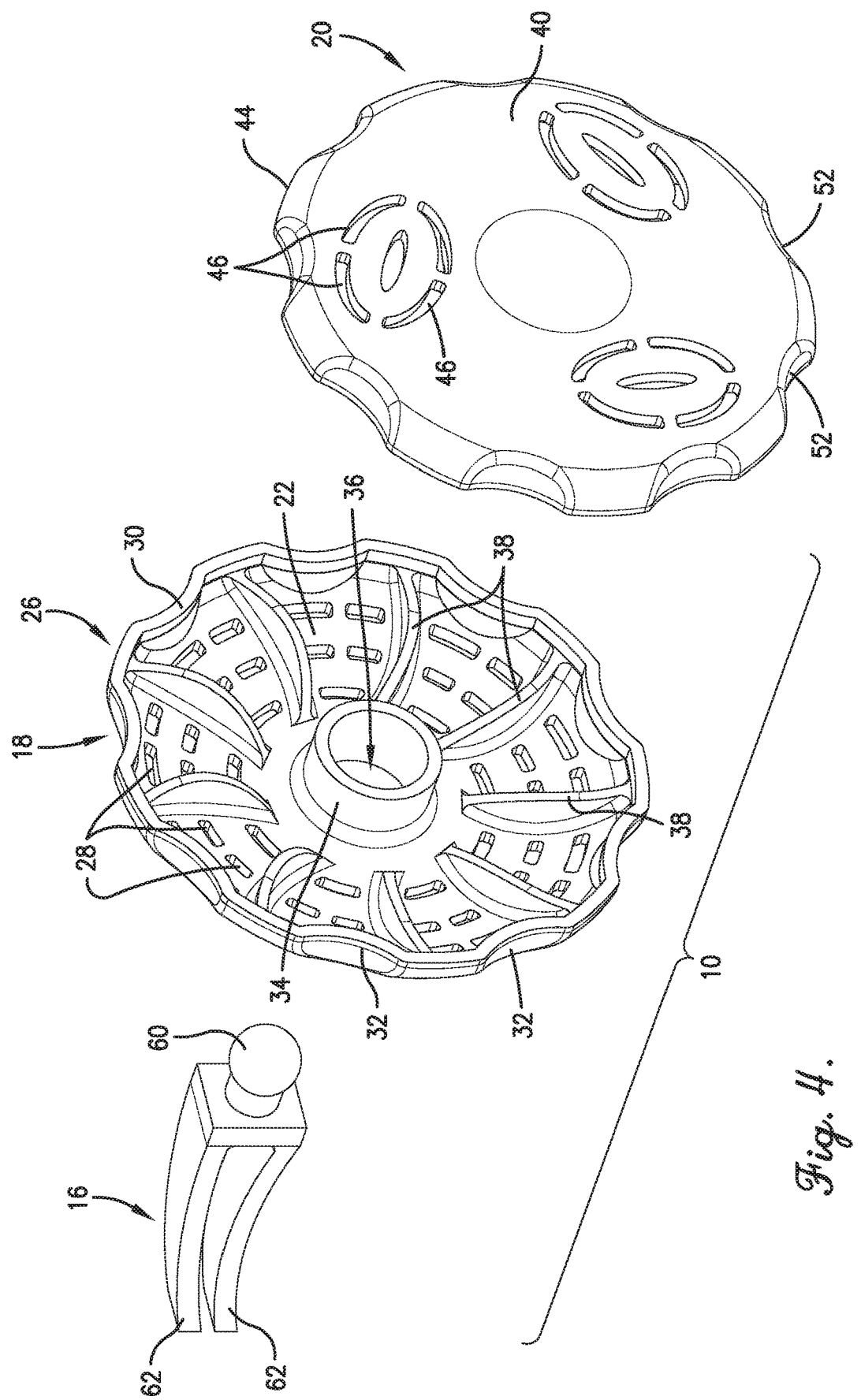
FIG. 4 is an exploded, front perspective view of the air freshener of FIG. 1.
Figure 7:
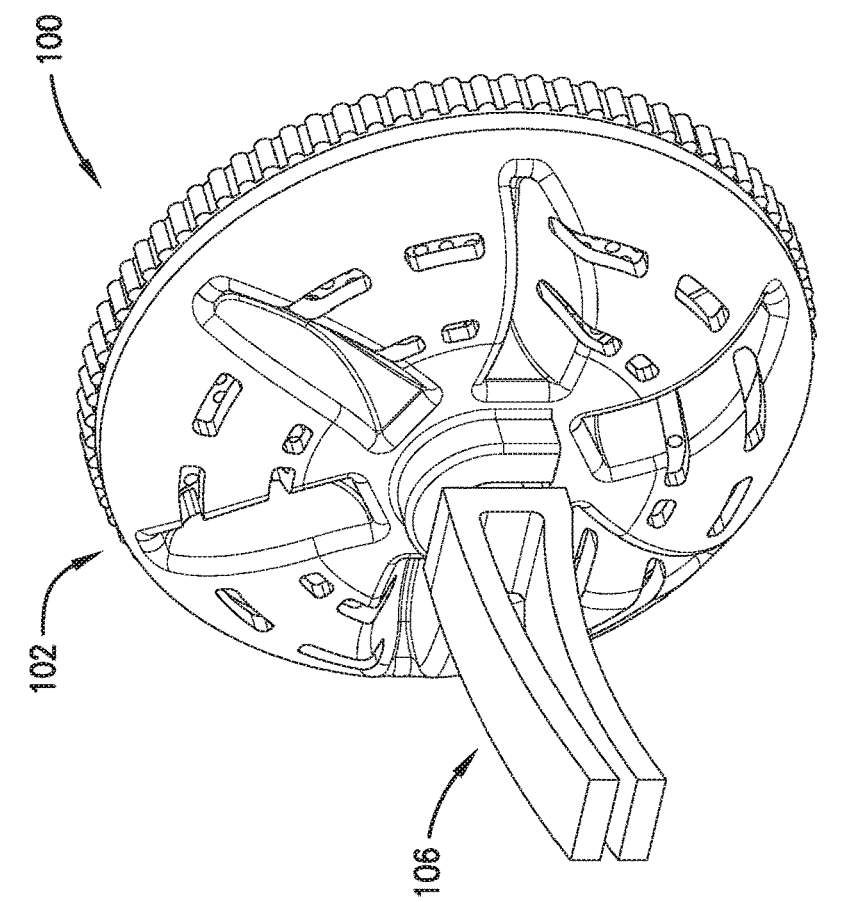
FIG. 7 is a rear perspective view of the air freshener of FIG. 6.
Figure 6:
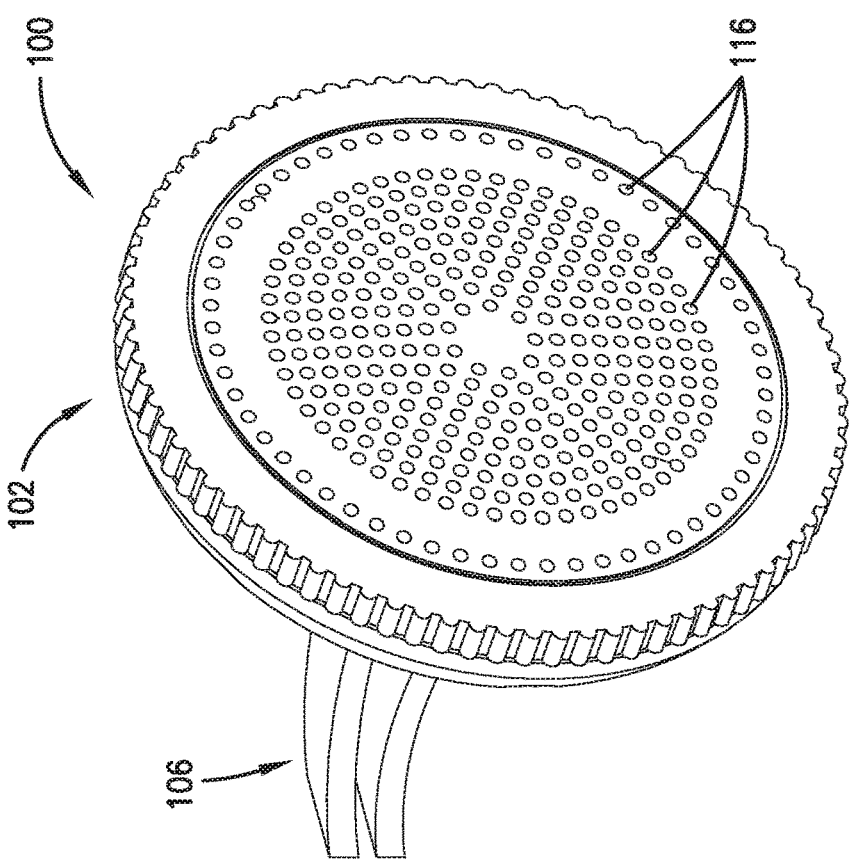
FIG. 6 is a front perspective view of an air freshener constructed in accordance with another embodiment of the present invention.

As best shown in FIG. 4, the rear housing section 18 also includes a raised cylindrical socket 34 that extends forward of its front face 24 and that defines a hollow passageway 36. The socket 34 serves as a connection point for the front housing section 20 and the mounting clip 16 as described in more detail below.

Referring again to FIG. 4, the rear housing section 18 also includes several mixing vanes 38 extending from of its front face, the purposes of which are described below. In one embodiment, nine spaced missing vanes 38 extend radially from the socket 34.

As best shown in FIGS. 4 and 5, the front housing section 20 includes front and rear faces 40, 42 and a sidewall 44 between the faces. Several airflow slots or openings 46 extend between the front and rear faces for permitting air to pass through the housing. The slots or openings are sized to retain the scented beads within the housing. In one embodiment, the slots or openings are arranged in three sets, with each set having a central oval-shaped opening surrounded by 4 spaced arcuate slots and occupy 10-40% of the surface area of the front face 40. In one embodiment, the slots 28 in the rear housing section 18 are bigger and/or more numerous than the slots 46 in the front housing section 20 so that, as pressurized air is blown into the housing, more air initially enters the housing then exits the housing. This pressurizes the housing to accelerate the evaporation of fragrance from the scented beads.

As best shown in FIG. 5, the sidewall 44 of the front housing section 20 includes a recessed lip 48 that defines an annular ledge 50 for mating with the outer lip 30 of the rear housing section. The sidewall also includes several spaced indents 52 that align with the indents 32 in the rear housing section 18 to facilitate gripping of the housing.

As best shown in FIG. 5, the front housing section 20 also includes a pair of locking tabs 54 extending from its rear face 42. The locking tabs may be pushed through the socket 34 on the rear housing section 18 to connect the two housing sections. The locking tabs 54 have enlarged radially-extending heads 56 that snap over the rear end of the socket 34 when the locking tabs 54 are pushed fully through the socket as best shown in FIG. 3.

The rear housing section also includes several mixing vanes 58 extending from its rear face 42, the purposes of which are described below. In one embodiment, three arcuate mixing vanes are provided, each positioned between the locking tabs and one set of the air flow openings 46.

The mounting clip 16 attaches the housing 12 to a source of pressurized air such as a vehicle air vent, fan, window blind, etc. Importantly, the mounting clip 16 is rotatably coupled to the rear housing section 18 so the housing 12 may be rotated relative to the mounting clip 16 and the air source to which it is attached as described in more detail below.

An embodiment of the mounting clip 16 includes a ball coupler 60 or similar coupler that may be urged in the rear of the socket 34 and between the locking tabs 54 in the socket. The locking tabs 54 retain the ball coupler in the socket and allow the ball coupler and rear housing section to rotate relative to one another. This allows the housing to be rotated in both clockwise and counterclockwise directions with no stops or limits of rotation. The mounting clip 16 also includes a pair of spaced connection arms 62 that may be placed over and straddle a louver of a vehicle air vent or other air source so the housing can be exposed to air flow from the air source and rotate relative to the air source.

The above-described air freshener 10 and similar embodiments of the air freshener may be used as follows. After it is removed from any packaging, the air freshener 10 may be clipped to a vehicle air vent or other air source with the mounting clip 16.

The air freshener provides several "levels" of fragrance. A first relatively low level of fragrance is always provided as fragrance evaporates from the scented beads 14 and exits the slots and openings 28, 46 in the housing 12. This low-level of fragrance is provided even when the housing 12 and enclosed beads 14 are not subjected to any pressurized air flow. A second relatively higher level of level of fragrance is provided when pressurized air is dispersed from the vehicle air vent or other air source and blows through and over the housing 12 and enclosed beads 14 to accelerate the evaporation of fragrance from the scented beads. This second level of fragrance is somewhat proportional to the rate of air flow (higher fan speeds provide greater fragrance).

A third level of level of fragrance can be achieved by rotating the housing 12 relative to the mounting clip 16 to cause the scented beads in the housing to tumble and release more fragrance. As the housing is rotated, the mixing vanes 38, 58 on the rear and front housing sections lift, stir, and drop the scented beads 14 to expose them to more air and thus increase the evaporation of fragrance from the beads. This provides an on-demand burst of fragrance when desired. The third level of fragrance is even greater if the housing is rotated while a pressurized air is blown over and through the housing. This third level of fragrance, which may be more or less than the second level of fragrance, is proportional to the rate at which the housing is rotated (faster spinning provides greater fragrance). This third level of fragrance also varies depending on whether the vehicle air vent or other air source is blowing air (fast spinning and high air flow releases the most fragrance).

An air freshener 100 constructed in accordance with an alternative embodiment of the invention is illustrated in FIGS. 6-10. The air freshener 100 is similar to the air freshener 10 of FIGS. 1-5 and broadly comprises a housing 102; scented beads 104 enclosed in the housing; and a mounting clip 106 for attaching the housing 102 to a vehicle air vent or other source of pressurized air.

As best illustrated in FIGS. 9 and 10, an embodiment of the housing 102 includes a rear housing section 108 and a front housing section 110. The rear housing section 108 is similar to the rear housing section 18 described above, the principal differences being the attachment mechanisms for the front housing section and the mounting clip. Specifically, the rear housing section 108 is attached to the front housing section 110 by a press-fit and/or adhesives rather than with the structures described above. And the rear housing section includes a U-shaped receiver slot 112 on its rear face for coupling with the mounting clip as described in more detail below. The rear housing section also includes larger and thicker mixing vanes 114, but fewer of them.

The front housing section 110 is similar to the front housing section 20 described above, the principal differences being its overall shape and the shape and arrangement of its air holes 116. Also, unlike the front housing section 20, the front housing section 110 does not include mixing vanes. Instead, the air freshener 100 relies on the larger and thicker mixing vanes 114 in the rear housing section 108 to lift, stir, and drop the scented beads when the housing is rotated.

Figure 8:
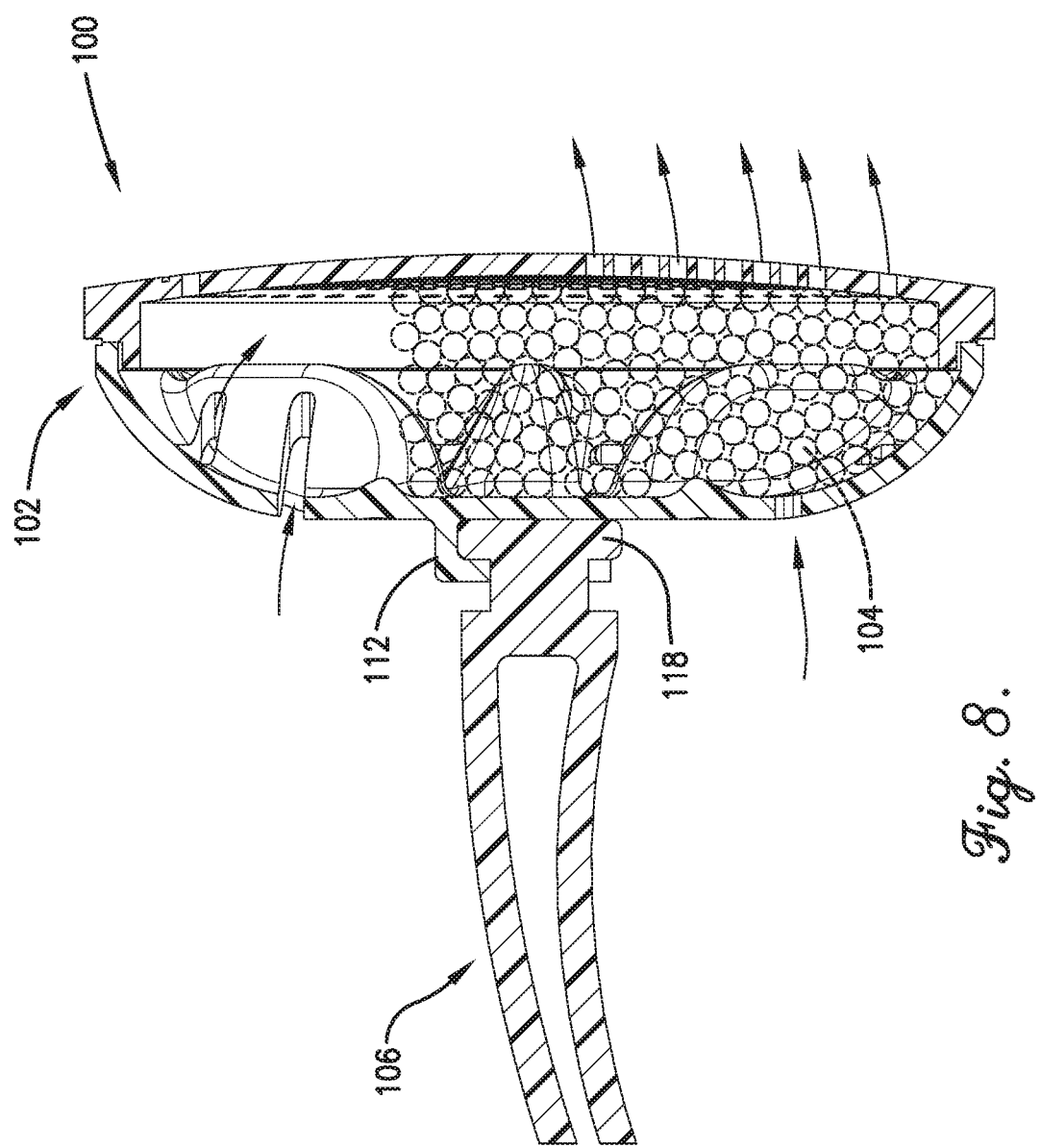
FIG. 8 is a vertical side sectional view of the air freshener of FIG. 6.

The mounting clip 106 is similar to the mounting clip 16 described above, the principal differences being its attachment mechanism. Rather than a ball coupler, the mounting clip includes a circular tab 118 that fits within and is rotatable relative to the receiver slot on the rear face of the rear housing section 108 as best illustrated in FIGS. 8 and 10.

ADDITIONAL CONSIDERATIONS

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the current technology can include a variety of combinations and/or integrations of the embodiments described herein.

Although the present application sets forth a detailed description of numerous different embodiments, the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The patent claims at the end of this patent application are not intended to be construed under 35 U.S.C. § 112(f) unless traditional means-plus-function language is expressly recited, such as "means for" or "step for" language being explicitly recited in the claim(s).

Although the invention has been described with reference to the embodiments illustrated in the attached drawing figures, it is noted that equivalents may be employed, and substitutions made herein without departing from the scope of the invention as recited in the claims.

Having thus described various embodiments of the invention, what is claimed as new and desired to be protected by Letters Patent includes the following:

1. A vehicle air freshener comprising:
   a partially hollow housing having—
      a number of airflow openings,
      a central portion,
      a sidewall surrounding the central portion,
      a front housing section and a rear housing section that together with the sidewall define a hollow chamber with a width,
      a first set of mixing vanes extending radially between the central portion and the sidewall, wherein portions of the first set of mixing vanes extend from the rear housing section at least halfway through the width of the hollow chamber, and
      a second set of mixing vanes extending from the front housing section and positioned around the central portion, wherein the second set of mixing vanes are arcuate comprising a convex side facing the central portion;
   scented beads enclosed in the housing so that the scented beads are operable to contact the first set of mixing vanes and the second set of mixing vanes; and
   a mounting clip coupled with the housing and attachable to a vehicle air vent so the housing and enclosed scented beads can be exposed to air flow from the air vent, the mounting clip and the housing having structure defining a ball joint so the housing may be manually rotated relative to the mounting clip and the air vent so the first set of mixing vanes and the second set of mixing vanes in the housing stir and tumble the scented beads in the housing to release fragrance from the scented beads.

2. The vehicle air freshener of claim 1, wherein the ball joint permits unlimited rotation of the housing relative to the mounting clip in clockwise and counter-clockwise directions.

3. The vehicle air freshener of claim 2, wherein the housing includes a socket and the mounting clip includes a ball mount contained in the socket.

4. The vehicle air freshener of claim 2, wherein the mounting clip further includes a pair of connection arms that may connect to the vehicle air vent.

5. The vehicle air freshener of claim 1, wherein the scented beads comprise plastic beads soaked in fragrant oil.

6. The vehicle air freshener of claim 1, wherein the rear housing section and front housing section are formed of plastic.

7. The vehicle air freshener of claim 1, wherein the rear housing section is disk-shaped and includes front and rear faces and several spaced airflow openings between the faces for permitting passage of air through the housing.

8. The vehicle air freshener of claim 1, wherein the front housing section is disk-shaped and includes front and rear faces and several spaced airflow openings between the faces for permitting passage of air through the housing.

9. The vehicle air freshener of claim 1, wherein the front housing section includes a plurality of airflow openings, wherein the second set of mixing vanes comprise a concave side positioned between at least one of the plurality of airflow openings and the central portion.

10. The vehicle air freshener of claim 1, wherein the first set of mixing vanes comprise at least 6 mixing vanes spaced apart around the central portion.

11. The vehicle air freshener of claim 1, wherein the first set of mixing vanes and the second set of mixing vanes together comprise at least 9 mixing vanes spaced apart around the central portion.

\* \* \* \* \*